(12) United States Patent
Turrou

(10) Patent No.: US 9,095,402 B2
(45) Date of Patent: Aug. 4, 2015

(54) ABSORBENT DEVICE FOR TEETH CLEANING AND ORAL SURGERY

(71) Applicant: Turrou Enterprises, LLC, Grand Junction, CO (US)

(72) Inventor: Robert Mason Turrou, Grand Junction, CO (US)

(73) Assignee: Turrou Enterprises, LLC, Grand Junction, CO (US)

( * ) Notice: Subject to any disclaimer, the term of this patent is extended or adjusted under 35 U.S.C. 154(b) by 194 days.

(21) Appl. No.: 13/841,885

(22) Filed: Mar. 15, 2013

(65) Prior Publication Data

US 2014/0272785 A1  Sep. 18, 2014

(51) Int. Cl.
| | |
|---|---|
| *A61F 13/15* | (2006.01) |
| *A61C 19/00* | (2006.01) |
| *A61D 5/00* | (2006.01) |
| *A61F 13/45* | (2006.01) |
| *A61F 13/64* | (2006.01) |
| *A61M 16/04* | (2006.01) |
| *A61C 17/06* | (2006.01) |

(52) U.S. Cl.
CPC .............. *A61C 19/001* (2013.01); *A61C 17/043* (2013.01); *A61D 5/00* (2013.01); *A61F 13/45* (2013.01); *A61F 13/64* (2013.01); *A61M 16/0434* (2013.01); *A61M 16/0497* (2013.01); *A61M 16/047* (2013.01); *A61M 2250/00* (2013.01)

(58) Field of Classification Search
CPC .. A61C 17/036; A61C 17/0203; A61C 17/22; A61C 17/00; A61C 17/005; A61C 17/046
USPC ............... 604/367, 368, 369; 433/136, 93, 94
See application file for complete search history.

(56) References Cited

U.S. PATENT DOCUMENTS

| | | | |
|---|---|---|---|
| 3,523,535 A | 8/1970 | Croon et al. | |
| 4,020,844 A | 5/1977 | Vickery | |
| 4,050,470 A | 9/1977 | Miller | |
| 4,233,025 A * | 11/1980 | Larson et al. | ................. 433/136 |
| 5,370,656 A | 12/1994 | Shevel | |
| 8,256,427 B2 | 9/2012 | Chang et al. | |
| 8,317,765 B2 | 11/2012 | Loyd et al. | |
| 2013/0014761 A1 | 1/2013 | Elia et al. | |

FOREIGN PATENT DOCUMENTS

| | | |
|---|---|---|
| CN | 201058076 | 5/2008 |
| EP | 1676552 | 2/2008 |
| RU | 20090105708 | 8/2010 |
| WO | 03032860 | 4/2003 |

OTHER PUBLICATIONS

International Search Report in PCT Application Serial No. PCT/US14/20429, mailed Jun. 5, 2014.

* cited by examiner

*Primary Examiner* — Jacqueline Stephens
(74) *Attorney, Agent, or Firm* — William W. Cochran; Cochran Freund & Young LLC

(57) ABSTRACT

Disclosed is an endotracheal tube having an absorbent device attached so that the absorbent device is able to absorb and block any procedure produced debris. The absorbent device has strings that are attached to a device around an endotracheal tube so that the absorbent device is properly dislodged at the end of the procedure.

8 Claims, 5 Drawing Sheets

ABSORBENT DEVICE FOR TEETH CLEANING AND ORAL SURGERY

BACKGROUND

Certain dental procedures require that a patient be placed under general anesthesia. These procedures may result in fluid, blood, tooth fragments, and other debris being produced. Dental procedures and routine dental cleanings are important steps in maintaining healthy oral hygiene.

SUMMARY

An embodiment of the invention may comprise a method of absorbing dental producing debris comprising: providing an absorbent device so that the absorbent device comprises an absorbent material in a ring shape defining a hole therethrough; providing strings that are securely attached to the absorbent device; providing an endotracheal tube that has a tracheal end and a connecting port end; sliding the absorbent device onto the endotracheal tube; releasably attaching the strings above a securing loop so that the securing loop is attached to the endotracheal tube.

An embodiment of the invention may further comprise a device for absorbing dental producing debris of a patient comprising: an endotracheal tube; a securing loop attached to the endotracheal tube; an absorbent device formed in an annulus having a substantially central opening that is adapted to allow insertion of the endotracheal tube and surrounds the endotracheal tube, the absorbent device being releasably attached to the endotracheal tube; strings securely attached to the absorbent device so that the absorbent device can be extracted from a trachea together with the endotracheal tube; a securing loop that securely attaches the endotracheal tube to the patient.

DETAILED DESCRIPTION OF THE EMBODIMENTS

Figure 1:
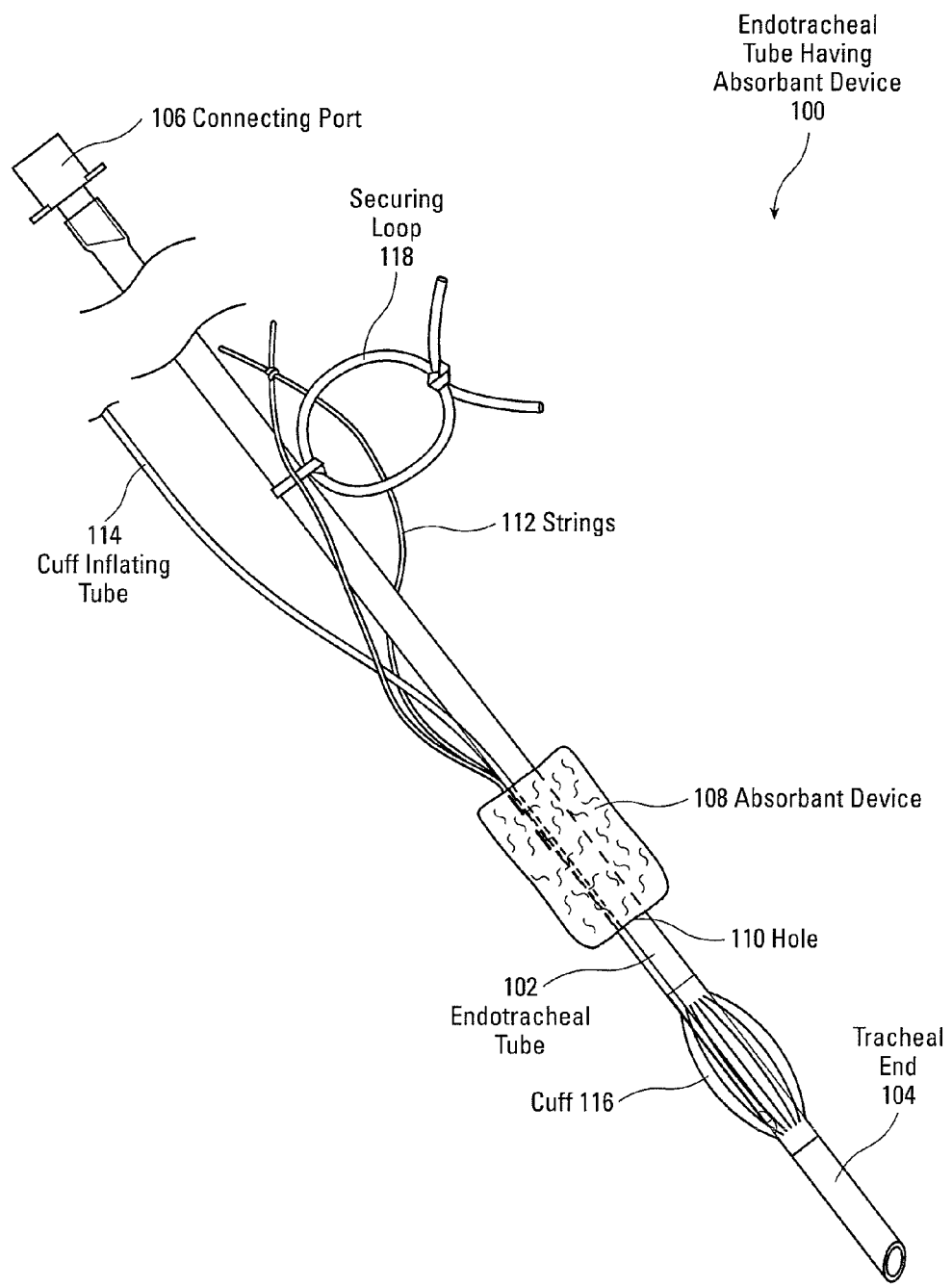
FIG. 1 is an isometric view of an endotracheal tube having an absorbent device.

FIG. 1 is an isometric view an endotracheal tube having an absorbent device 100. During surgery and teeth cleaning, or any dental procedure that produces debris, there can be accidental inhalation of debris, for example, tartar and blood, that can endanger the patient. It should be noted that a patient is defined as including, but not limited to animals, humans and any other creatures that benefit from the disclosed endotracheal tube having an absorbent device 100. Endotracheal tube having absorbent device 100 is used to prevent such debris from any dental procedure produced debris from reaching the pharynx. In other words, during anesthesia for veterinary dental procedures or human oral surgery Endotracheal tube having absorbing device 100 occludes the back of the throat (oropharynx) and absorbs liquids thereby preventing accidental inhalation of debris such as, but not limited to tartar and blood after the endotracheal tube 102 is removed, but before the patient has fully regained their protective reflex to not inhale anything into their lungs via the trachea except for air. Many veterinarians and oral surgeons have been taught to pack the back of a patient's throat with gauze sponges or ribbon gauze during dental anesthesia. However, the gauze must be remembered to be removed at the end of a procedure when a patient is awakening, otherwise, the gauze can either occlude the opening to the trachea or can be inhaled into the trachea resulting in asphyxiation, or can be swallowed thereby possibly needing removal of the swallowed object from the gastrointestinal tract by endoscopy or surgery. Some surgeons tie colored strings or sutures to the gauze sponges as to help them remember to remove the sponges later. Endotracheal tube having absorbent device 100 eliminates this problem which will be discussed later.

Returning to FIG. 1, endotracheal tube 102 has tracheal end 104 and connecting port 106. Tracheal end 104 of endotracheal tube 102 is inserted into the patient's trachea so that absorbent device 108 is lodged in a patient's oropharynx so that absorbent device 108 is able to block and/or absorb blood, fluid and any other debris, so that a patient does not swallow or inhale any dental procedure produced debris. Absorbent device 108 is placed on endotracheal tube 102 via hole 110. Absorbent device 108 has strings 112, which are looped around the endotracheal tube 102 proximal to (or above) securing loop 118. Endotracheal tube has a cuff inflating tube 114, which inflates cuff 116. Cuff inflating tube 114 and cuff 116 are not required for endotracheal tube 102 to function properly. However, cuff 116 may be employed as an extra measure to seal off the trachea and also to ensure that absorbent device 108 remains secured on endotracheal tube 102 when being removed from a patient's trachea, so that absorbent device 108 does not slide off of tracheal end 104 of endotracheal tube 102. However, cuff 116 is not required because strings 112 are also looped around the endotracheal tube above (proximal to) securing loop 118. Connecting port 106 of endotracheal tube 102 connects to breathing hoses of anesthetic machine during anesthesia. Alternatively, strings 112 may be attached to something outside of the mouth to ensure absorbent device is removed with endotracheal tube 102 at the end of anesthesia.

Figure 2:
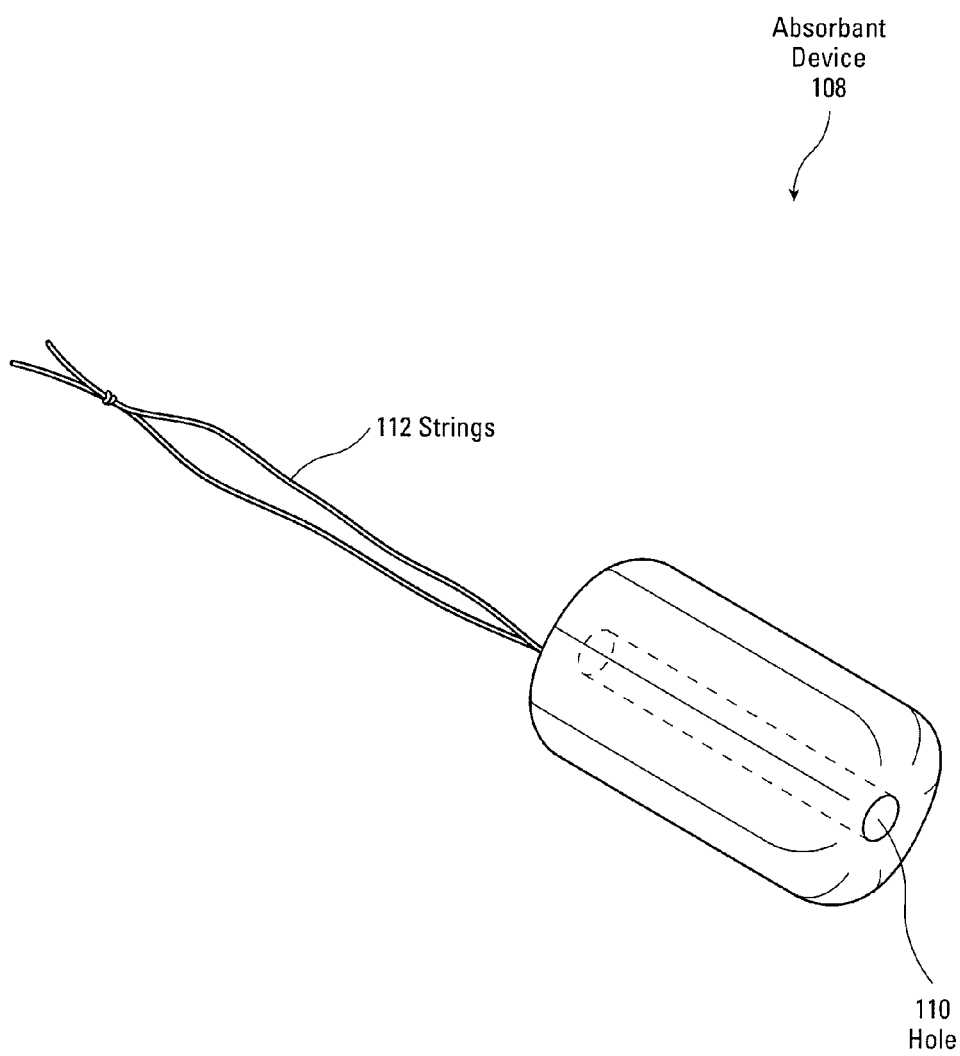
FIG. 2 is an isometric view of the absorbent device of FIG. 1.

FIG. 2 is an isometric side view of absorbent device 108 that was shown in FIG. 1 attached to endotracheal tube 102. Absorbent device has hole 110, which travels through the entire absorbent device 108. FIG. 2 also shows strings 112 that are attached to absorbent device 108.

Figure 3:
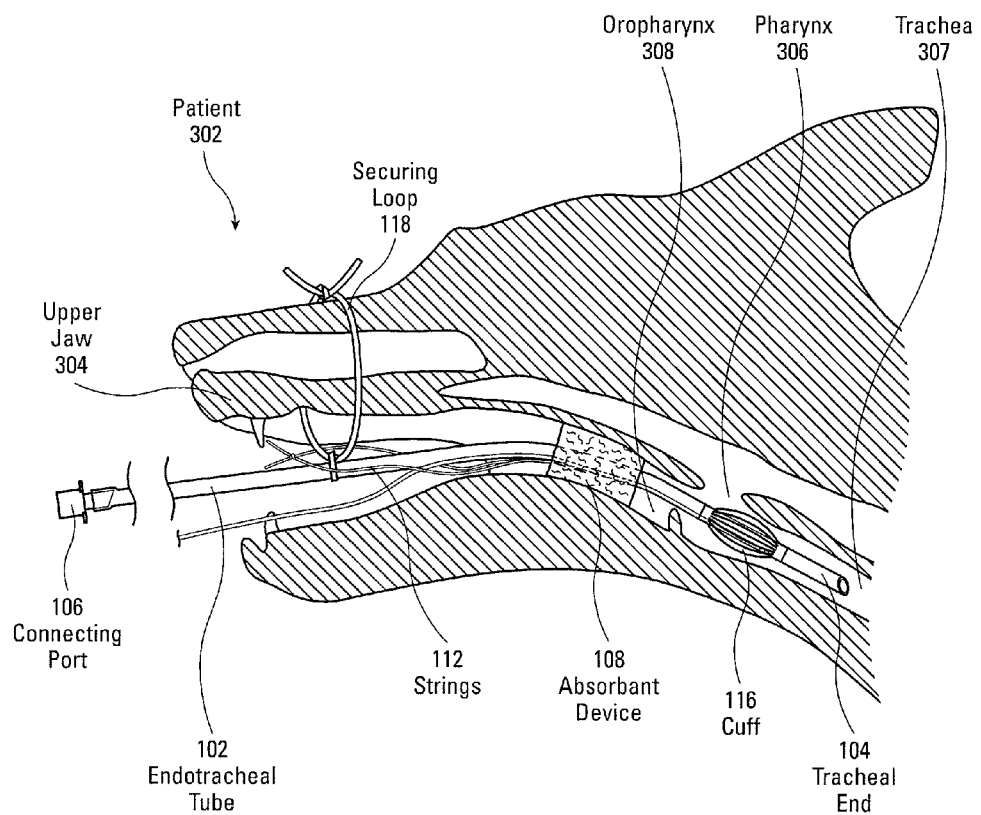
FIG. 3 is an isometric side view of an endotracheal tube having an absorbent device secured to an upper jaw.

FIG. 3 shows patient 302 having an upper jaw 304 and pharynx 306. Patient 302 has endotracheal tube 102 disposed in the trachea 307, so that tracheal end 104 of endotracheal tube 102 is lodged in trachea 307 and connecting port 106 of endotracheal tube 102 is able to connect to anesthetic machine breathing hoses. Absorbent device 108 of endotracheal tube 102 has strings 112, that are looped above (or proximal to) securing loop 118, and securing loop 118 is securely attached around the upper jaw 304 of animal. During a dental procedure, which could result in debris being produced, absorbent device 108 blocks and/or absorbs fluid, blood and other debris, so that such debris does not travel down patient 302 pharynx 306. In other words, absorbent device 108 swells when in contact with fluid thereby effectively occluding the oropharynx 308, preventing any dental procedure produced debris from reaching pharynx 306 or trachea 307. At the end of a procedure, securing loop 118 is removed from upper jaw 304, thereby disengaging endotracheal tube 102 having absorbent device 108 from patient 302 oropharynx 308. The positioning of securing loop 118, around upper jaw 304 that has strings 112 looped above securing loop 118 ensures absorbent device 108 is automatically extracted from oropharynx 308 when endotracheal tube 102 is removed from patient 302. Although cuff 116 is not required, cuff 116 can assist in absorbent device 108 being properly removed from oropharynx 308. In other words, although not required, cuff 116 is an extra precautionary measure to ensure that absorbent device 108 will not slide off of tracheal end 104 of endotracheal tube 102.

Figure 4:
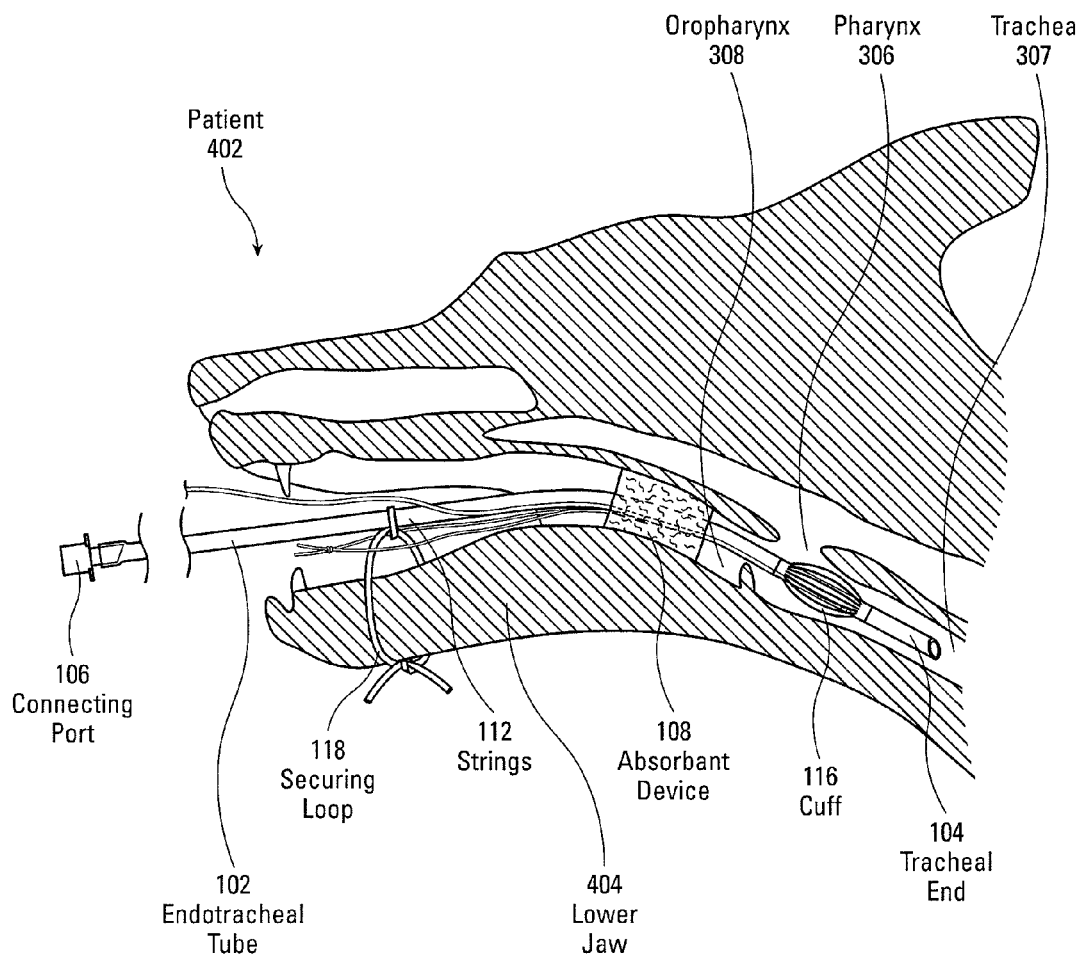
FIG. 4 is an isometric view of an endotracheal tube having an absorbent device secured to a lower jaw.

FIG. 4 shows patient 402 having a lower jaw 404. Patient 402 has endotracheal tube 102 inserted into trachea 307, so that tracheal end 104 of endotracheal tube 102 is positioned in trachea 307 and connecting port 106 of endotracheal tube 102 is able to connect to anesthetic machine breathing hoses. Absorbent device 108 of endotracheal tube 102 has strings 112, which are looped proximal to securing loop 118, and securing loop 118 is securely attached to lower jaw 404. During a dental procedure, which could result in debris being produced, absorbent device 108 blocks and/or absorbs fluid, blood and other debris, so that such debris does not travel down to back of patient 402 pharynx 306. In other words, absorbent device 108 swells when in contact with fluid, thereby effectively occluding the oropharynx 308, thereby preventing any dental procedure produced debris from reaching pharynx 306. At the end of a procedure, securing loop 118 is removed from lower jaw 404, thereby disengaging endotracheal tube 102 having absorbent device 108 from patient 402 oropharynx 308. The positioning of securing loop 118, around lower jaw 404 that has strings 112 looped above securing loop 118 ensures absorbent device 108 is automatically extracted from oropharynx 308 when endotracheal tube 102 is removed from patient 402. Although cuff 116 is not required, cuff 116 can assist in absorbent device 108 being properly removed from oropharynx 308. In other words, although not required, cuff 116 is an extra precautionary measure to ensure that absorbent device 108 will not slide off of tracheal end 104 of endotracheal tube 104.

Figure 5:
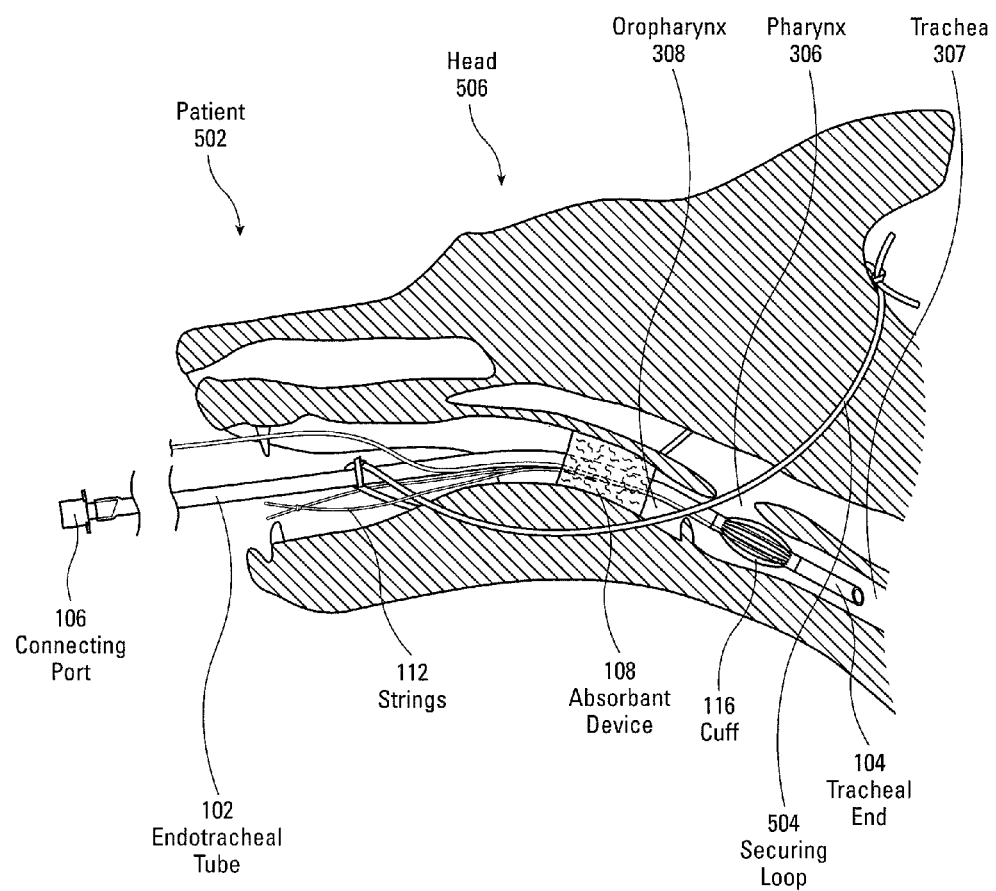
FIG. 5 is an isometric view of an endotracheal tube having an absorbent device secured to the back of a head.

FIG. 5 shows patient 502 having a head 506 and pharynx 306. Patient 502 has endotracheal tube 102 disposed in the trachea 307, so that tracheal end 104 of endotracheal tube 102 is lodged in trachea 307 and connecting port 106 of endotracheal tube 102 is able to connect to anesthetic machine breathing hoses. Absorbent device 108 of endotracheal tube 102 has strings 112, that are looped above (or proximal to) securing loop 118, and securing loop 118 is securely attached around the back of the head 506 of patient 502. During a dental procedure, which could result in debris being produced, absorbent device 108 blocks and/or absorbs fluid, blood and other debris, so that such debris does not travel down patient 302 pharynx 306. In other words, absorbent device 108 swells when in contact with fluid thereby effectively occluding the oropharynx 308, preventing any dental procedure produced debris from reaching pharynx 306 or trachea 307. At the end of a procedure, securing loop 118 is removed from the head 506, thereby disengaging endotracheal tube 102 having absorbent device 108 from patient 502 oropharynx 308. The positioning of securing loop 118, around the back of the head 506 that has strings 112 looped above securing loop 118 ensures absorbent device 108 is automatically extracted from oropharynx 308 when endotracheal tube 102 is removed from patient 502. Although cuff 116 is not required, cuff 116 can assist in absorbent device 108 being properly removed from oropharynx 308. In other words, although not required, cuff 116 is an extra precautionary measure to ensure that absorbent device 108 will not slide off of tracheal end 104 of endotracheal tube 102.

It should be noted that all embodiments disclosed in FIGS. 3-5 may encompass any type of animal. In other words, the embodiment of FIG. 3 is not limited to dogs and can encompass any animal including but not limited to a human. Similarly, the embodiments of FIGS. 4 and 5 may encompass any type of patient wherein patient is defined as an animal or human.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A method of absorbing dental producing debris in a patient comprising:
   providing an absorbent device so that said absorbent device comprises an absorbent material in a ring shape defining a hole therethrough;
   providing strings that are securely attached to said absorbent device which assist in removing said absorbent device from said patient;
   providing an endotracheal tube that has a tracheal end and a connecting port end;
   placing said absorbent device around said endotracheal tube between said connecting port end and said tracheal end at a location that is proximate to said tracheal end and disposed in an oropharynx of said patient when said endotracheal tube is disposed in said patient, so that said absorbent device completely surrounds said endotracheal tube and engages said oropharynx of said patient;
   providing a cuff on said endotracheal tube that is disposed between said absorbent device and said tracheal end of said endotracheal tube, said cuff assisting in removing said absorbent device from said patient by providing an enlarged portion on said endotracheal tube that engages said absorbent device when said endotracheal tube is removed from said patient;
   releasably attaching said strings above a securing loop so that said securing loop is attached to said endotracheal tube.

2. The method of claim 1 further comprising:
   attaching said securing loop to an upper jaw of a patient.

3. The method of claim 1 further comprising:
   attaching said securing loop to a lower jaw of a patient.

4. The method of claim 1 further comprising:
   attaching said securing loop around the back of a patient's head.

5. A device for absorbing dental producing debris of a patient comprising:
   an endotracheal tube having a tracheal end and a connecting port end;
   a securing loop attached to said endotracheal tube;
   an absorbent device formed in an annulus having a substantially central opening that is adapted to allow insertion of said endotracheal tube so that said absorbent device completely surrounds said endotracheal tube, said absorbent device being releasably attached to said endotracheal tube;

a cuff disposed on said endotracheal tube between said tracheal end and said absorbent device, said cuff assisting in removing said absorbent device from said patient by providing an enlarged portion on said endotracheal tube that engages said absorbent device when said endotracheal tube is removed from said patient;

strings securely attached to said absorbent device so that said absorbent device can be extracted from a trachea together with said endotracheal tube;

a securing loop that securely attaches said endotracheal tube to said patient.

6. The endotracheal tube of claim 5 wherein said securing loop is attached to a patient's upper jaw.

7. The endotracheal tube of claim 5 wherein said securing loop is attached to a patient's lower jaw.

8. The endotracheal tube of claim 5 wherein said securing loop is securely attached around the back of a patient's head.

* * * * *